(12) United States Patent
Verreet

(10) Patent No.: US 8,254,660 B2
(45) Date of Patent: Aug. 28, 2012

(54) METHOD AND DEVICE FOR INSPECTING A TRAVELING WIRE CABLE

(75) Inventor: Roland Verreet, Aachen (DE)

(73) Assignee: Casar Drahtseilwerk Saar GmbH, Kirkel (DE)

(*) Notice: Subject to any disclaimer, the term of this patent is extended or adjusted under 35 U.S.C. 154(b) by 975 days.

(21) Appl. No.: 12/083,415

(22) PCT Filed: Oct. 13, 2006

(86) PCT No.: PCT/EP2006/009908
§ 371 (c)(1),
(2), (4) Date: Apr. 11, 2008

(87) PCT Pub. No.: WO2007/045403
PCT Pub. Date: Apr. 26, 2007

(65) Prior Publication Data
US 2009/0232383 A1 Sep. 17, 2009

(30) Foreign Application Priority Data
Oct. 20, 2005 (DE) .......................... 10 2005 050 220

(51) Int. Cl.
*G06K 9/00* (2006.01)
(52) U.S. Cl. ...................................................... 382/141
(58) Field of Classification Search .................... 382/141
See application file for complete search history.

(56) References Cited

U.S. PATENT DOCUMENTS

| 3,599,223 A | | 8/1971 | Bridenbaugh et al. | |
| 3,718,976 A | * | 3/1973 | Nippert, Sr. | 33/743 |
| 3,761,177 A | | 9/1973 | Corse | |
| 4,887,155 A | * | 12/1989 | Massen | 348/88 |

FOREIGN PATENT DOCUMENTS

| DE | 197 42 177 | 4/1999 |
| EP | 0 271 728 | 6/1988 |
| EP | 0 565 906 | 10/1993 |

* cited by examiner

*Primary Examiner* — Tarifur Chowdhury
*Assistant Examiner* — Jonathon Cook
(74) *Attorney, Agent, or Firm* — Lucas & Mercanti, LLP; Klaus P. Stoffel

(57) ABSTRACT

In a first embodiment, a picture is taken of the traveling wire cable in a stationary position at intervals that are equal to the ratio produced from the lay length or a multiple of the lay length and the travel speed of the wire cable, at least op one lay length or the above-mentioned multiple of the lay length, and the successive images are compared on at least one lay length or the above-mentioned multiple of the lay length and are monitored for changes in the image which are indicative of damages. In a second embodiment, the wire cable is instead of taking pictures exposed to flashes and the exposed image is detected on at least one lay length or the above-mentioned multiple of the lay length and monitored for changes in the image. Preferably, the respective repetition of the same outer stranded wire of the traveling wire cable is detected in the same location and every repetition or every other repetition or every third repetition is used for triggering the taking of a picture or for triggering the flash. In a third embodiment, a picture is taken of a large portion of the wire cable using a specialized camera and the image is split up into recurring units of length that correspond to the size of a lay length or a multiple of the lay length and the successive units of length are compared and inspected for changes in the image.

11 Claims, 3 Drawing Sheets

2 cm

METHOD AND DEVICE FOR INSPECTING A TRAVELING WIRE CABLE

BACKGROUND OF THE INVENTION

The invention relates to a method for inspecting a traveling wire cable.

It further relates to a device for carrying out the method.

Wire cables per se are to be examined visually on a daily basis for wire breaks and the occurrence of other faults. This cannot be carried out in practice. In order to be examined, the wire cable must be stationary or travel very slowly, and the work must be interrupted.

Magnetoinductive wire cable testing on traveling cables is possible, but complicated.

SUMMARY OF THE INVENTION

It is the object of the invention to make available a further, simple method for inspecting a traveling wire cable.

In accordance with the invention, it is provided in a first version that the traveling wire cable is photographed at a stationary position at time intervals that are equal to the quotient of the lay length or a multiple of the lay length, and the travel speed of the wire cable, at least on one lay length or said multiple of the lay length, and the successive pictures are compared at least on one lay length or said multiple of the lay length, and are monitored for changes in the image that indicate damage.

In a second version, it is provided that the traveling wire cable is illuminated with light flashes at a stationary position at time intervals that are equal to the quotient of the lay length, or a multiple of the lay length, and the travel speed of the wire cable, at least on a lay length or said multiple of the lay length, and the illuminated image is detected at least on a lay length or said multiple of the lay length, and is monitored for changes in the image that indicate damage.

The twisted strands of a wire cable appear again after one lay length at the same position of the cable circumference. Successive sections of the wire cable of the size of the lay length therefore exhibit the same strand picture, each strand lies again at the same position. This then likewise holds for sections whose size is a multiple of the lay length.

The wire picture within the strands is displaced in this case, as a rule. It remains exactly the same, that is to say each wire lies again at the same position, only when the lay length of the wires in the strand are at a specific ratio to the lay length of the strands in the cable. It remains apparently the same when the wires are displaced by exactly one wire thickness or an integral multiple of the wire thickness.

If a traveling wire cable is always photographed or flashed by a camera arranged in a stationary fashion, or a stroboscope arranged in a stationary fashion whenever exactly one lay length or a multiple of the lay length has traveled past, the image photographed, or the image rendered visible against a sufficiently darker background by the light flashes is always the same. Starting from a specific frequency (image frequency approximately 24 per second), the images merge in front of the eye to form an uninterrupted image.

A "still image" of the strands is produced. The wires within the strands "migrate" slowly as a rule, and the strands seem to rotate about their own axis.

Damage in the wire cable causes a variation that is very quickly over, mostly cannot be detected pictorially, but is perceptible, or a visible change in the migratory movement of the wires.

The eye does not become tired when viewing the invariable or slowly migrating image. If a variation is perceived, the fault thereby discovered is examined in more detail later.

The variant of the flash illuminations is provided chiefly for immediate, direct viewing with the eye.

The variant of photographing likewise later permits viewing with the eye.

However, it can also be automized in a fashion ranging from partially to completely.

According to an advantageous refinement of the invention, the respective return of the same outer strand of the traveling wire cable at the same position is detected, and each, or each second or third, return is used to trigger shooting or the light flash.

Consequently, the correct instant for the next picture or flash illumination is respectively ensured in a simple way, even when there is a change in the time intervals when starting up or braking the wire cable, or for other reasons such as certain changes in lay length over the length of a hanging cable.

However, there are also other possibilities in principle. For example, the travel speed of the wire cable can be picked off at the drive of the drive pulley of the cable, and said quotient can be constantly recalculated by a computer and the time sequence of the shootings or light flashes can be correspondingly controlled. If there is also a change in the lay length, this can be acquired with the aid of a separate lay length transmitter and also be input for the purpose of calculating the quotient.

The return of the strand is expediently acquired by detecting all the strands, preferably by means of a proximity sensor responding to the strand bulge, and by counting the strands. That is to say, in the case, for example, of six strands in the outer ply each sixth strand bulge belongs to the same ply and triggers the shooting or the light flash. If the cable feed is simultaneously measured between the return of the same strand, this information can be used to establish a possible variation in lay length as a function of the cable length. It can be advantageous in this case to acquire the return of the same strand with the aid of a number of sensors arranged in an offset fashion. It can be established in this way whether, for example, the intervals between two successive perceptions of the same strand have been shortened by an actual shortening of the cable lay length or by a twisting of the cable between the sensor positions.

According to a further refinement of the invention, the return of the strand is acquired by detecting a marking of the strand.

By way of example, the marking can be optical, for example it can consist of copper plating or of a magnetization, or can be a radioactive marking. To this extent, the invention also covers the production of wire cables that are prepared from the start to be inspected later.

This also holds for the further proposal of respectively marking a wire of the outer strands in a visible fashion, in order to render the migration of the wires in the strands visible in a more effective fashion.

According to a further refinement of the invention, the detection of the return of the same strand of the traveling wire cable is, furthermore, used, by recording the return of the strand or recording the bulge, to track the position of the wire cable that is respectively located at said stationary position, and to record the location of damaged positions on the wire cable starting therefrom.

This would also be possible, however, by means of a separate position pickup.

The damaged positions can then be examined more accurately later.

The length of the wire cable detected in the image need not be limited to a lay length or said multiple of the lay length. If it is larger, a fault can simply appear twice in the image. This need not, however, result in irritation, but can even lead to enhancing the perception.

An advantageous refinement of the mode of procedure consists in that on the basis of a change perceived in the acquired image the relevant damaged position is photographed with a high resolution camera at a position lying downstream of said stationary position in the travel direction of the wire cable.

When making a direct visual examination, it is possible if appropriate also immediately to run the wire cable backward and search for and examine the damaged position.

As a rule, the method is carried out simultaneously from various sides in order to detect the entire cable circumference.

A device for carrying out the method has in a station traversed by the wire cable a camera that is directed onto the wire cable and is connected to a controller; an evaluation and recording device is connected to the camera.

As a rule, the camera or photocell is multiply present and is directed onto the wire cable from various sides in order to detect the circumference of the wire cable completely.

The controller and the evaluation and recording device are preferably common to the various cameras or photocells.

Finally, in a third version of the invention it is provided that the traveling wire cable is photographed on a large length and the picture is decomposed into recurring length units for example of the size of a lay length or a multiple of the lay length, and the successive length units are compared and examined for changes in the image that indicate damage.

The decomposition, aimed at the possibility of shooting the entire wire cable, into the length units can be undertaken by a manual method or, preferably, automatically with the aid of a computer. The length units can then be further processed in the same way as if they had, as described above, resulted directly as a sequence of images from repeated triggering of the camera.

In order to produce an image, preferably a digital one, in the width of the cable diameter and in the length of the entire cable, it is possible, for example, to apply the same technique of exposure by a slit-shaped diaphragm as is used when taking analog or digital panorama photos. All that remains is to swing the camera or the lens; the image section imaged by the slit is varied by the travel of the wire cable itself. It is necessary only to synchronize the speed of the camera with the cable speed.

BRIEF DESCRIPTION OF THE DRAWINGS

The aim below is to explain the invention further with the aid of drawings, in which.

DETAILED DESCRIPTION OF THE INVENTION

Figure 1:
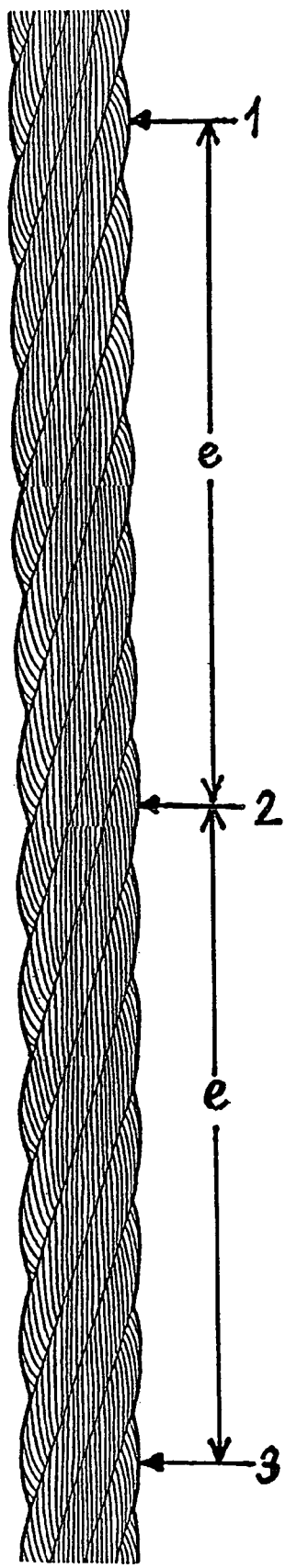
FIG. 1 shows a section of a wire cable.

In FIG. 1, the arrows 1, 2 and 3 point to the successive occurrence of the same strand at the same 25 position, offset in each case by the lay length e, of the cable circumference of a wire cable 10. The same strands in the same configuration are visible between the arrows 1 and 2 and between the arrows 2 and 3.

Figure 2:
FIG. 2 shows a section of FIG. 1.

This configuration is illustrated per se in FIG. 2.

Figure 3:
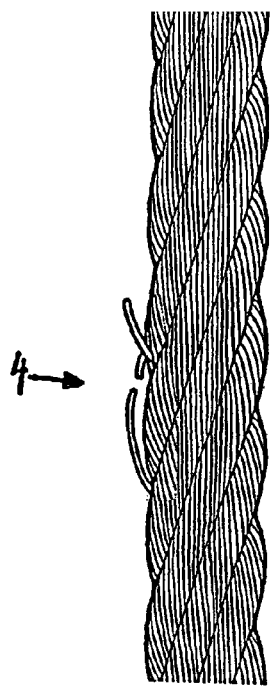
FIG. 3 shows a second section, corresponding to FIG. 2.
Figure 4:
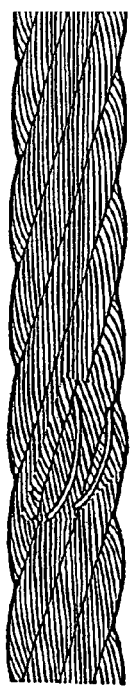
FIG. 4 shows a third section, corresponding to FIG. 2.
Figure 5:
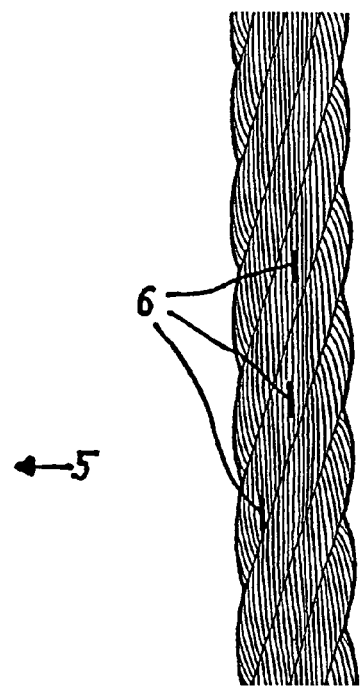
FIG. 5 shows a fourth section, corresponding to FIG. 2.

It is respectively illustrated once again in FIGS. 3, 4 and 5, there with wire breaks 4 and 5 and 6, respectively. The wire breaks 4 and 5 are illustrated exaggeratedly. At the wire breaks 6, the wire has merely retracted somewhat and left a gap that has filled with dirt and lubricant and is to be recognized as a short dark line.

Figure 6:
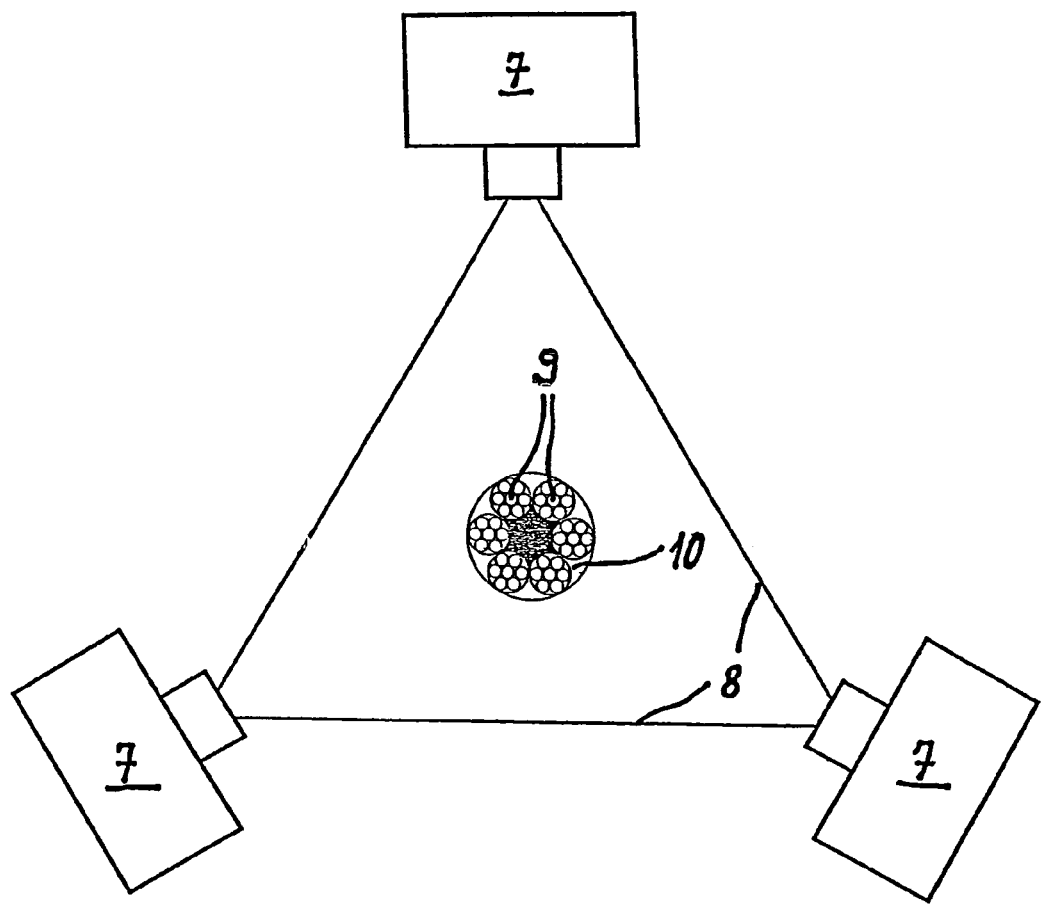
FIG. 6 shows, schematically as an exemplary embodiment, a device for inspecting a traveling wire cable.

FIG. 6 shows a station with three camera 7 directed onto the wire cable 10 from various sides. Lines 8 mark the regions acquired by the cameras 7.

The lay length of the strands 9 of the wire cable 10 is 250 mm in the present example, the travel speed of the wire cable 10 perpendicular to the plane of the drawing is 5 m/sec, and the flash frequency of the camera is 20 hertz. That is to say, the wire cable is photographed at intervals of 0.05 sec whenever the next section of the wire cable of the size of the lay length is located in front of the cameras 7.

For the rest, reference may be made to the explanations given further above.

The invention claimed is:

1. A method for inspecting a traveling wire cable, wherein the traveling wire cable is photographed at a stationary position at time intervals that are equal to the quotient of the lay length or a multiple of the lay length, and the travel speed of the wire cable, at least on one lay length or said multiple of the lay length, so that the pictures show structure of the wire cable and twisted strands of the wire cable appear in the pictures in the same position of the cable circumference, the pictures being successively reproduced in an image and the pictures are compared with each other, and the image is monitored for changes in the cable structure that indicate damage.

2. The method as claimed in claim 1, wherein the respective return of the outer strand of the traveling wire cable at the same position is detected, and each, or each second or third, return is used to trigger shooting or a light flash.

3. The method as claimed in claim 2, wherein the return of the strand is acquired by detecting all the strands, preferably by means of a proximity sensor responding to the strand bulge, and by counting the strands.

4. The method as claimed in claim 2, wherein the return of the strand is acquired by detecting a marking of the strand.

5. The method as claimed in claim 2, wherein recording the return of the strand, or recording the bulge, tracks the position of the wire cable that is respectively located at said stationary position, and the location of damaged positions on the wire cable is recorded starting therefrom.

6. The method as claimed in claim 1, wherein it is provided for inspecting wire cables in which respectively one wire of the outer strands is visibly marked.

7. The method as claimed in claim 1, wherein on the basis of a change perceived in the acquired image the relevant damaged position is photographed at a position lying downstream of said stationary position in the travel direction of the wire cable.

8. The method as claimed in claim 1, wherein it is carried out simultaneously from various sides.

9. A device for carrying out a method as claimed in claim 1, wherein in a station traversed by the wire cable (10) a camera (7) is directed onto the wire cable (10) and is connected to a controller, and an evaluation and recording device is connected to the camera, the controller controls the camera (7) so that the traveling wire cable (10) is photographed at one lay length or multiple of the lay length at time intervals that are equal to the quotient of the lay length or the multiple of the lay length and the travel speed of the wire cable, the evaluation and recording device being operative to compare wire cable structure in the pictures successively reproduced in an image, and to monitor the image for changes in the cable structure that indicate damage.

10. The device as claimed in claim 9, wherein the camera (7) consists of a plurality of cameras (7) directed onto the wire cable (10) from various sides.

11. The device as claimed in claim 10, wherein the controller and the evaluation and recording device are common to the cameras (7).

* * * * *